US010894268B2

(12) United States Patent
Ou

(10) Patent No.: US 10,894,268 B2
(45) Date of Patent: Jan. 19, 2021

(54) ULTRASONIC ESSENTIAL OIL ATOMIZER

(71) Applicant: FOSHAN SHUNDE ULTEK ELECTRIC APPLIANCE CO., LTD, Foshan (CN)

(72) Inventor: Ying-Gang Ou, Foshan (CN)

(73) Assignee: FOSHAN SHUNDE ULTEK ELECTRIC APPLIANCE CO., LTD, Foshan (CN)

( * ) Notice: Subject to any disclaimer, the term of this patent is extended or adjusted under 35 U.S.C. 154(b) by 457 days.

(21) Appl. No.: 15/768,551

(22) PCT Filed: Mar. 29, 2018

(86) PCT No.: PCT/CN2018/081076
§ 371 (c)(1),
(2) Date: May 31, 2018

(87) PCT Pub. No.: WO2019/148625
PCT Pub. Date: Aug. 8, 2019

(65) Prior Publication Data
US 2019/0232319 A1 Aug. 1, 2019

(30) Foreign Application Priority Data
Feb. 1, 2018 (CN) .......................... 2018 1 0103094

(51) Int. Cl.
*A61L 9/00* (2006.01)
*B05B 1/08* (2006.01)
*B05B 17/06* (2006.01)

(52) U.S. Cl.
CPC ................................ *B05B 17/0607* (2013.01)

(58) Field of Classification Search
CPC ... A61L 9/00; A61L 9/04; A61L 9/012; A61L 2101/32; A61L 9/013; A61L 2209/132; A61L 9/14; B05B 17/0615; A61M 11/005
(Continued)

(56) References Cited

U.S. PATENT DOCUMENTS 9,511,166 B1 * 12/2016 Li .......................... A61M 11/06
2017/0274405 A1 * 9/2017 Lucas ...................... A61L 9/14

* cited by examiner

*Primary Examiner* — Monzer R Chorbaji
(74) *Attorney, Agent, or Firm* — IP Trust

(57) ABSTRACT

The present invention discloses an ultrasonic essential oil atomizer, which includes an ultrasonic energy conversion device, having an energy conversion sheet and a driving circuit electrically connected to the energy conversion sheet, wherein a working voltage of the driving circuit is below 8V; at least one oiler, disposed on the ultrasonic energy conversion device and having a connection portion and an oil guiding cavity communicating with the connecting portion, wherein a nozzle is disposed at the bottom of the oil guiding cavity and the nozzle is disposed on a surface of the energy conversion sheet; and at least one essential oil bottle, having a bottle body and an inner lid, wherein the bottle body has a cavity and a bottle mouth communicating with the cavity, the inner lid includes a lid portion and an air intake portion disposed at a side of the lid portion, the lid portion is disposed on the bottle mouth, the bottle mouth is connected to the connection portion, an oil outlet and an air inlet are disposed on the lid portion, the oil outlet communicates with the cavity and the oil guiding cavity, the air inlet is disposed at a side of the oil outlet and communicates with the air intake portion, and the air intake portion extends to an interior of the cavity and is further communicating with the interior of the cavity. The ultrasonic essential oil atomizer may achieve the atomization of the water-soluble and non-water-soluble essential oils, and has a function for automatically replenishing the essential oil, with simple structure and the small size.

10 Claims, 11 Drawing Sheets

(58) Field of Classification Search
USPC ..... 422/5, 20, 127–128, 305–306; 239/102.2
See application file for complete search history.

ULTRASONIC ESSENTIAL OIL ATOMIZER

BACKGROUND

Technical Field

The present invention is related to an atomizer technical field, and more particular to an ultrasonic essential oil atomizer.

Related Art

The ultrasonic energy conversion sheet has advantages of high conversion efficiency for converting the power energy to the mechanical energy, smaller volume, high performance-to-price ratio, and working with no-noise, and thus it is widely used in the household humidifiers. In the household humidifiers, the energy conversion sheet is generally installed on the bottom of a water body and driven by the electronic circuits. When working in water, the water is atomized through the cavitation and then evaporated to the air. Most of the heat generated during work is carried away through the water cycle, so as to maintain the temperature rise of the energy conversion sheet in a reasonable range. In general, the working voltage of the household humidifiers is 36V or 24V. Under the working voltage, if there is no water or liquid on the surface of the energy conversion sheet, only a few seconds, the temperature of the energy conversion sheet may rise sharply to 140° C. or more. The high temperature may cause a corresponding high temperature risk. Due to the high temperature effect, the energy conversion sheet may have a problem of the magnetic loss such that the efficiency for converting the power energy to the mechanical energy seriously declines, and the liquid may not be atomized. In other word, currently, since the heat generation during the working of the ultrasonic energy conversion sheet is more serious, in order to maintain the temperature rise of the energy conversion sheet in a reasonable range, it is generally required that the surface of the energy conversion sheet works in water or liquid, so as to achieve the requirement of the heat dissipation while working and to prevent the working temperature from being too high (i.e., dry burning), which results in greatly shortening the service life of the energy conversion sheet and the occurrence of the high temperature to risk. Therefore, if it is desirous to use the energy conversion sheet to atomize the essential oil directly, it is necessary to solve the problem of heat dissipation when the energy conversion sheet works at a high frequency.

SUMMARY

In view of the deficiencies of the prior art, the present invention provides an ultrasonic essential oil atomizer.

An ultrasonic essential oil atomizer provided by the present invention includes: an ultrasonic energy conversion device, having an energy conversion sheet and a driving circuit electrically connected to the energy conversion sheet, wherein a working voltage of the driving circuit is below 8V;

at least one oiler, disposed on the ultrasonic energy conversion device and having a connection portion and an oil guiding cavity communicating with the connecting portion, wherein a nozzle is disposed at the bottom of the oil guiding cavity and the nozzle is disposed on a surface of the energy conversion sheet; and at least one essential oil bottle, having a bottle body and an inner lid, wherein the bottle body has a cavity and a bottle mouth communicating with the cavity, the inner lid includes a lid portion and an air intake portion disposed at a side of the lid portion, the lid portion is disposed on the bottle mouth, the bottle mouth is connected to the connection portion, an oil outlet and an air inlet are disposed on the lid portion, the oil outlet communicates with the cavity and the oil guiding cavity, the air inlet is disposed at a side of the oil outlet and communicates with the air intake portion, and the air intake portion extends to an interior of the cavity and further communicates with the interior of the cavity.

According to one embodiment of the present invention, the ultrasonic energy conversion device further includes a heat sink, wherein the heat sink includes a thermal grease and a fin radiator, the thermal grease is disposed under the energy conversion sheet, and the fin radiator is disposed under the thermal grease.

According to one embodiment of the present invention, a distance between the nozzle and a center point of the energy conversion sheet is 1 mm to 4 mm.

According to one embodiment of the present invention, a distance between the nozzle and the surface of the energy conversion sheet is 0.1 mm to 0.5 mm.

According to one embodiment of the present invention, the lid portion includes a lid body and an oil outlet portion, wherein the lid body has an cylindrical cavity with hollow interior and a bottom lid, the bottom lid is disposed at one end of the cylindrical cavity, an air inlet and an oil outlet are disposed on the bottom lid, the air inlet communicates with an interior of the cylindrical cavity, the oil outlet portion is disposed inside the cylindrical cavity and communicates with the oil outlet and the oil guiding cavity, respectively.

According to one embodiment of the present invention, the ultrasonic energy conversion device further includes a bracket, wherein the bracket includes a supporting portion and a limiting portion connected to the supporting portion, the connection portion of the oiler is disposed inside the supporting portion, and the oil guiding cavity of the oiler passes through the supporting portion and extends to the limiting portion.

According to one embodiment of the present invention, the ultrasonic energy conversion device includes a housing, the housing includes a first case and a second case oppositely disposed; the first case is provided with a first seat, a second seat, a third seat and a fourth seat in order from top to bottom, two ends of the casing wall of the first case are respectively provided with a block, the second housing is provided with a fifth seat, a sixth seat, a seventh seat and a eighth seat respectively corresponding to the first seat, the second seat, the third seat, and the fourth seat from top to bottom, two ends of the casing wall of the second case are respectively provided with a seat slot, the blocks of the first case is disposed in the seat slot of the second case, the limiting portion is disposed inside the first seat and the fifth seat, the energy conversion sheet is disposed inside the second seat and the sixth seat, the heat sink is disposed inside the third seat and the seventh seat, and the driving circuit is disposed inside the fourth seat and the eighth seat.

According to one embodiment of the present invention, the driving circuit includes a starting switch, a low-voltage power circuit, an energy conversion sheet high frequency oscillating circuit and a controlling chip, and the starting switch, the low-voltage power circuit, the energy conversion sheet high frequency oscillating circuit are respectively electrically connected to the controlling chip, wherein the low-voltage power circuit provides a direct current power to the controlling chip, the starting switch provides a starting signal, the controlling chip outputs a high frequency signal to the energy conversion sheet high frequency oscillating circuit according to the starting signal, the energy conversion sheet high frequency oscillating circuit provides a high frequency driving signal to the energy conversion sheet, and the energy conversion sheet is oscillated according to the high frequency driving signal.

According to one embodiment of the present invention, the oiler further includes a sealing ring, and the sealing ring is disposed between the inner lid and the connection portion of the oiler.

An ultrasonic essential oil atomizer provided by the present invention includes:

an ultrasonic energy conversion device, having an energy conversion sheet and a driving circuit electrically connected to the energy conversion sheet, wherein a working voltage of the driving circuit is below 8V;

a plurality of oilers, disposed on the ultrasonic energy conversion device, wherein each of the oilers includes a connection portion and an oil guiding cavity communicating with the connecting portion, a nozzle is disposed at the bottom of the oil guiding cavity and the nozzle is disposed on a surface of the energy conversion sheet; and a plurality of essential oil bottles, each of the essential oil bottles having a bottle body and an inner lid, wherein the bottle body has a cavity and a bottle mouth communicating with the cavity, the inner lid includes a lid portion and an air intake portion disposed at a side of the lid portion, the lid portion is disposed on the bottle mouth, the bottle mouth is connected to the connection portion, an oil outlet and an air inlet are disposed on the lid portion, the oil outlet communicates with the cavity and the oil guiding cavity, the air inlet is disposed at a side of the oil outlet and communicates with the air intake portion, and the air intake portion extends to an interior of the cavity and further communicates with the interior of the cavity.

In the present invention, the working voltage of the driving circuit of the ultrasonic energy conversion device is below 8V. The ultrasonic essential oil atomizer works at a low voltage, and the voltage drop reduces when the energy conversion sheet operates at the high frequency. Even if there is continuous dry burning in air, the temperature rise would not exceed 60° C. (140° F.), such that the high temperature risk and the magnetic loss risk are reduced. When the energy conversion sheet works, the temperature rise is low, the essential oil to be atomized may be directly carried on the surface of the energy conversion sheet for direct atomization, such that the ultrasonic essential oil atomizer achieves the atomization of the water-soluble and non-water-soluble essential oils. In the atomization process, the structure of the inner structure of the essential oil bottle and the physical principle of the gravity of the essential oil itself are used, the natural formation and the thickness control of the liquid film of the essential oil are achieved.

The ultrasonic essential oil atomizer has an automatic replenishing function, thereby ensuring that the appropriate amount of the essential oil flowing out from the bottle body of the essential oil bottle covers the surface of the energy conversion sheet and the essential oil may also be continuously replenished to the energy conversion sheet from the bottle body. The structure for automatically replenishing the essential oil is simple and the cost is low. The high efficiency of the atomization and the continuous work requirement are achieved, such that the ultrasonic essential oil atomizer maintains the atomization working state with the high efficiency.

In the present invention, the ultrasonic essential oil atomizer has at least one energy conversion sheet, one or more oilers and one or more essential oil bottles. When the amount of the energy conversion sheet is at least one and the amount of the essential oil bottle and oiler is more than one, each of the essential oil bottle may be filled with the same or different essential oils. The same or different essential oils are respectively conveyed to the surface of the same energy conversion sheet or the surface of one of the corresponding different energy conversion sheets through an oiler correspondingly disposed. The driving circuit converts the power energy to the mechanical energy, such that one energy conversion sheet oscillates or the multiple energy conversion sheets simultaneously oscillate, and the essential oil is atomized and then diffuses and evaporates in the air. Therefore, two or more types of essential oils may be simultaneously atomized.

BRIEF DESCRIPTION OF THE DRAWINGS

The drawings described herein are used to provide a further understanding of the present invention and form a part of the present invention. The schematic embodiments and the descriptions of the present invention are used to explain the present invention and do not constitute improper limitations to the present invention.

DETAILED DESCRIPTION

Various embodiments of the present invention will be disclosed below by way of illustration, and for the sake of clarity, many practical details will be described in the following description. However, it should be understood that these practical details should not be used to limit the present invention. That is, in some embodiments of the present invention, these practical details are not necessary. Additionally, in order to simplify the drawings, some conventional structures and components will be illustrated in a simplified and schematic manner.

Additionally, the description of "first", "second" and the like in the present invention is merely for the purpose of description and are not intended to be indicate the order or the sequence, nor are they intended to limit the present invention. It is merely for distinguishing components or actions described in the same technical terms.

Three embodiments are used to describe the structure and operation principle of the ultrasonic essential oil atomizer of the present invention in details as follows, so as to explain the detailed technical solutions and benefits for overcoming the problem of heat dissipation during an energy conversion sheet working at the high frequency in details.

Embodiment I

Figure 1:
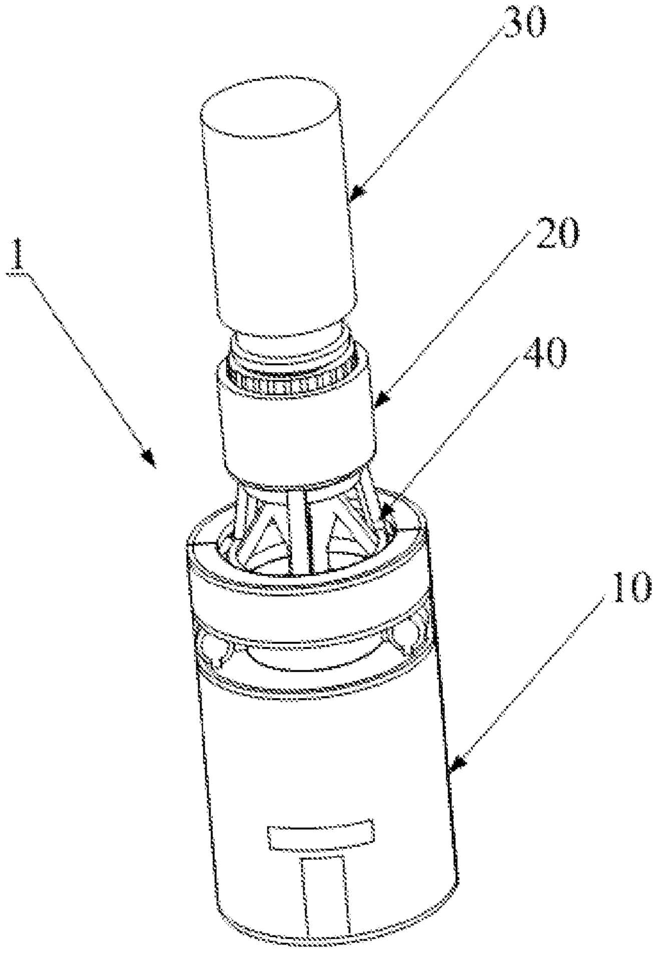
FIG. 1 is a stereogram of an ultrasonic essential oil atomizer according to Embodiment I of the present invention.
Figure 2:
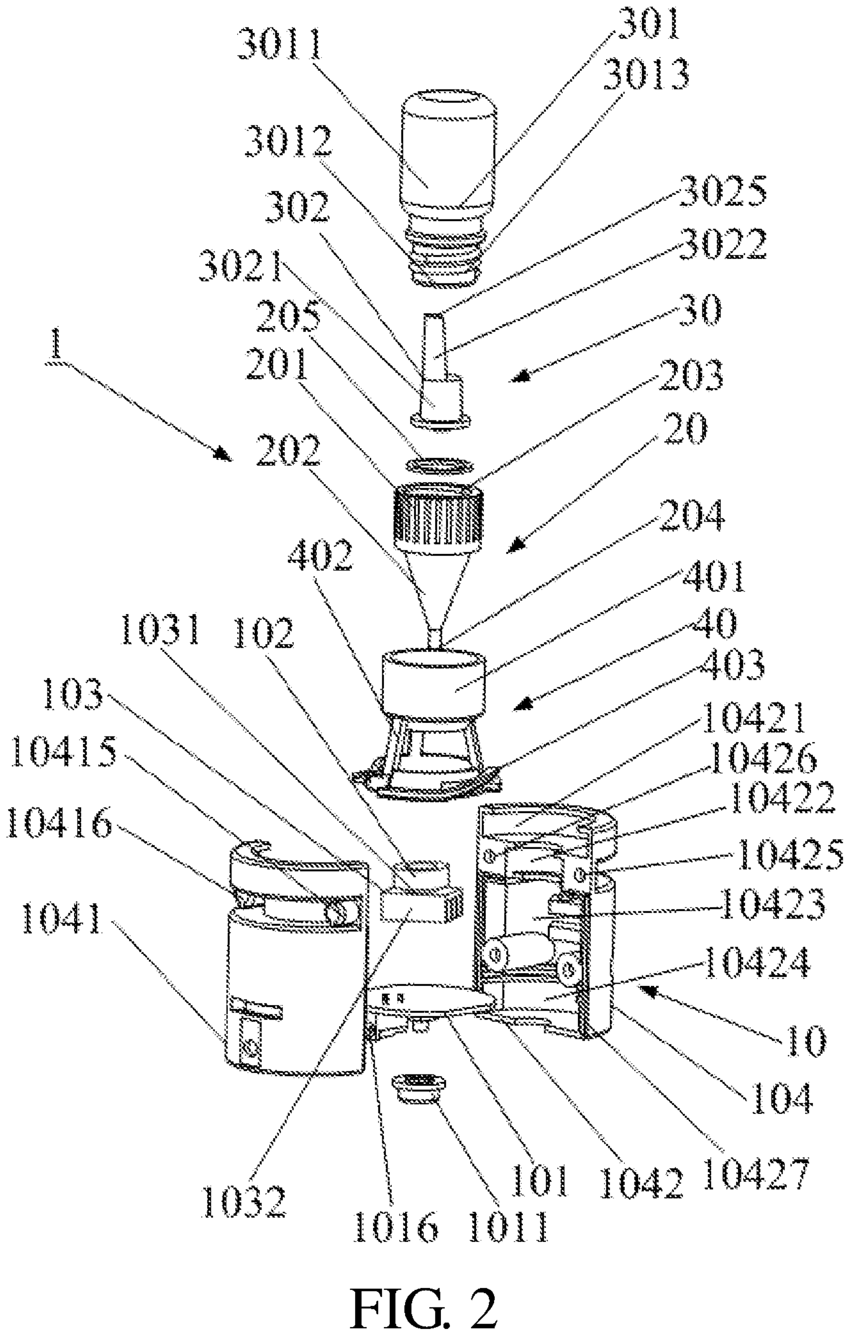
FIG. 2 is an explosion diagram of an ultrasonic essential oil atomizer according to Embodiment I of the present invention.

Referring to FIGS. 1 and 2, FIG. 1 is a stereogram of an ultrasonic essential oil atomizer according to Embodiment I of the present invention; FIG. 2 is an explosion diagram of an ultrasonic essential oil atomizer according to Embodiment I of the present invention. As shown in the figures, the present invention provides an ultrasonic essential oil atomizer 1. The ultrasonic essential oil atomizer 1 of the present invention includes an ultrasonic energy conversion device 10, an oiler 20 and an essential oil bottle 30. The oiler 20 is disposed on the ultrasonic energy conversion device 10 and the essential oil bottle 30 is disposed on the oiler 20. When the essential oil to be atomized is filled in the essential oil bottle 30, the essential oil flows into the oiler 20 under gravity, the oiler 20 conveys the essential oil to be atomized to the ultrasonic energy conversion device 10, and the ultrasonic energy conversion device 10 converts a power energy to a mechanical energy and atomize the essential oil.

Figure 3:
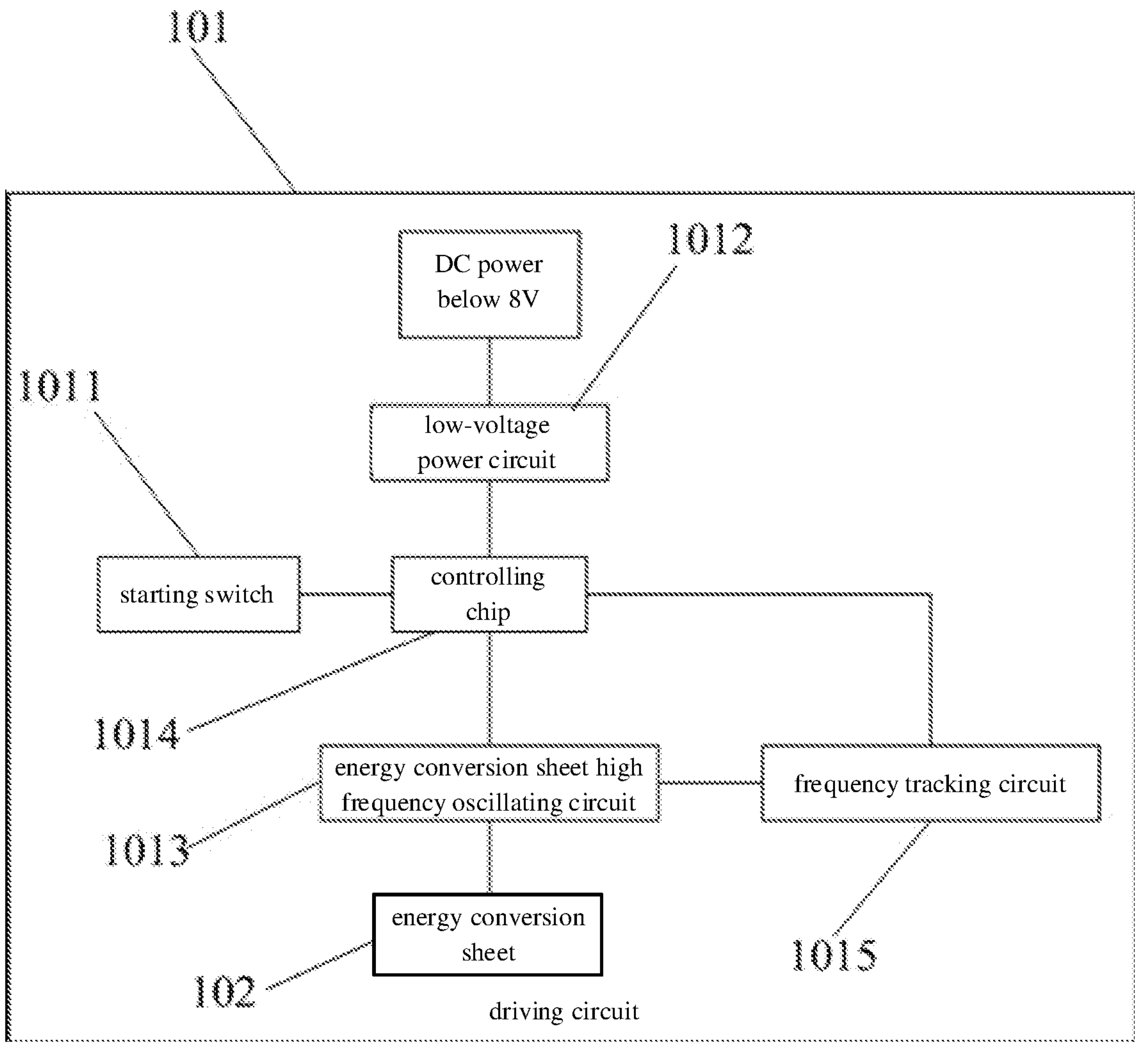
FIG. 3 is a block diagram of a driving circuit according to Embodiment I of the present invention.

The structure of the ultrasonic energy conversion device 10, the oiler 20 and the essential oil bottle 30 of the present invention is described in details as follows. The ultrasonic energy conversion device 10 of the present invention includes a driving circuit 101 and an energy conversion sheet 102, and the driving circuit 101 and the energy conversion sheet 102 are electrically connected. The driving circuit output a high frequency driving signal to the energy conversion sheet, and the energy conversion sheet oscillates according to the high frequency driving signal, wherein a working voltage of the driving circuit is below 8V, preferably the working voltage is 5V. Please refer to FIG. 3. FIG. 3 is a block diagram of the driving circuit 101. The driving circuit 101 includes a starting switch 1011, a low-voltage power circuit 1012, an energy conversion sheet high frequency oscillating circuit 1013 and a controlling chip 1014. The starting switch 1011, the low-voltage power circuit 1012, the energy conversion sheet high frequency oscillating circuit 1013 are respectively electrically connected to the controlling chip 1014. When the ultrasonic essential oil atomizer works, a direct current power is inputted to the low-voltage power circuit 1012, the low-voltage power circuit 1012 converts the inputted direct current power and outputs the converted power to the controlling chip 1014, the starting switch provides a starting signal, the controlling chip 1014 outputs a frequency signal to the energy conversion sheet high frequency oscillating circuit 1013 according to the starting signal, the energy conversion sheet high frequency oscillating circuit 1013 generates a high frequency driving signal to the energy conversion sheet 102, and the energy conversion sheet 102 is oscillated according to the high frequency driving signal. Further, the driving circuit further includes a frequency tracking circuit 1015, and the frequency tracking circuit 1015 is electrically connected to the energy conversion sheet high frequency oscillating circuit 1013 and the controlling chip 1014, respectively. The frequency tracking circuit 1015 collects a voltage signal of the energy conversion sheet 102 and converts the voltage signal of the energy conversion sheet 102 to a current signal, and the controlling unit 1014 obtains an oscillating frequency of the energy conversion sheet 102 according to the current signal. The driving circuit 101 is further provided with a DC power socket 106 connected to the direct current power below 8V. Further, the controlling chip 1014 further stores a controlling program, and the controlling program is used to control the energy conversion sheet high frequency oscillating circuit 1013 to convert the high frequency signal to the mechanical energy for outputting according to a predetermined time. Therefore, the ultrasonic essential oil atomizer 1 does not require the continuous working, and takes an intermittent working mode instead. That is, the ultrasonic atomizing oil device 1 stops atomizing after working for the predetermined time, and stops for the predetermined time and then re-atomizes.

For a problem that the energy conversion sheet 102 generates a large amount of heat when working at the voltage of 36V or 24V, in the embodiment, the working voltage of the driving circuit 101 is below 8V. A lower voltage, which is below 8V, is used as the input voltage for working. The working peak voltage of the energy conversion sheet 102 is not high, and a voltage drop is reduced during working at the high frequency. Even if there is continuous dry burning in air, the heat rise is lower than the traditional working voltage at 36V or 24V. In the air at room temperature, the balance of heat dissipation may be achieved. The service life of the transducer plate 102 may be extended, and the atomization effect may be ensured. That is, in the embodiment, the working voltage within a certain range is used to make the energy conversion sheet 102 for dry burning, so as to achieve the atomization working of the energy conversion sheet 102 at a low voltage through separately excited driving circuit. The separately excited driving circuit has low generated heat, suitable to work at low voltage power supply. Additionally, the concentration of the essential oil is generally large. The ultrasonic essential oil atomizer adopts an intermittent working mode, i.e. stops atomizing after working for a period of time, and stops for the period of time and then re-atomizes. In this way, the working mode with work-stop cycle causes the heat of the energy conversion sheet 102 to be less concentrated, and the consumption time of essential oils is also effectively extended.

Figure 4:
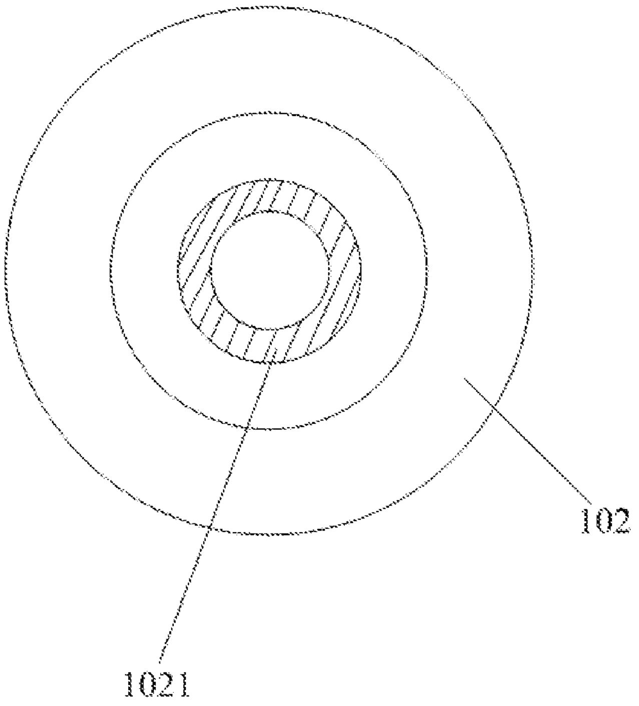
FIG. 4 is a schematic view of a position that a nozzle is disposed according to Embodiment I of the present invention.

Please continue referring FIGS. 1 and 2. The oiler 20 is disposed on the ultrasonic energy conversion device 10 and the oiler 20 is generally made of silica gel or metal. The silica gel may withstand a certain temperature and does not scratch the surface of the energy conversion sheet 102. The oiler 20 includes a connection portion 201 and an oil guiding cavity 202. The connecting portion 201 communicates with the oil guiding cavity 202. The internal wall of the connecting portion 201 is provided with internal threads 203. The oil guiding cavity 202 is funnel-shaped. A nozzle 204 is disposed at the bottom of the oil guiding cavity 202. The nozzle 204 is disposed on a surface of the energy conversion sheet 102. The oiler 20 further includes a sealing ring 205, and the sealing ring 205 is disposed between the essential oil bottle 30 and the connection portion 201 of the oiler 20. When the essential oil is atomized, the essential oil flows to the surface of the energy conversion 102. The liquid surface is required to be as thin as possible, and the thin liquid surface makes the essential oil is atomized more finely and float farther when the energy conversion sheet 102 works. If the liquid surface is too thick, the energy conversion sheet 102 may only make the essential oil into droplets and can not atomize the essential oil to diffuse into the air. Therefore, in the embodiment, a distance between the nozzle 204 and a center point of the energy conversion sheet 102 is 0.1 mm to 0.5 mm. When the essential oil flows to the nozzle 204 through the oil guiding cavity 202, the essential oil may form a thin layer on the nozzle 204 under tension, such that the atomization of the essential oil is finer. If the distance between the nozzle 204 and a center point of the energy conversion sheet 102 is far, the essential oil flows in the form of droplets to the energy conversion sheet 102, such that the liquid surface is thicker, and the essential oil can not be fully atomized to diffuse in the air. In addition, in the embodiment, as shown in FIG. 4, FIG. 4 is a schematic view of a position that a nozzle is disposed. The nozzle 204 is installed in an annular band area 1021 within 1 mm to 4 mm from the center point of the energy conversion sheet 102. When the energy conversion sheet 102 works, microscopically, it moves along the axial direction of the energy conversion sheet 102. When the nozzle 204 is disposed in the annular band area 1021 within 1 mm to 4 mm from the center point of the energy conversion sheet 102, the disposing position of the nozzle 204 does not affect the amplitude of the energy conversion sheet 102 and may make the nozzle to be located at a region that the amplitude of the energy conversion sheet 102 is larger, so as to ensure the atomization effect of the essential oil.

Figure 5:
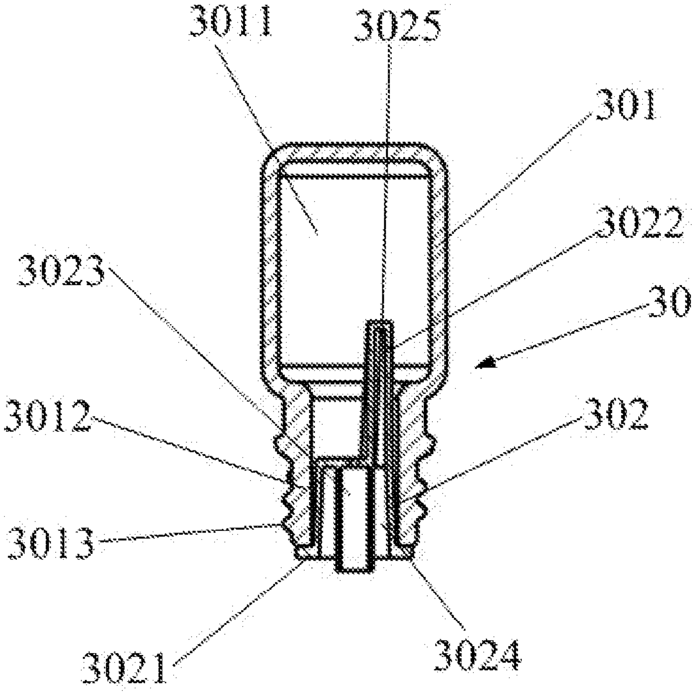
FIG. 5 is a sectional view of an essential oil bottle according to Embodiment I of the present invention.
Figure 6:
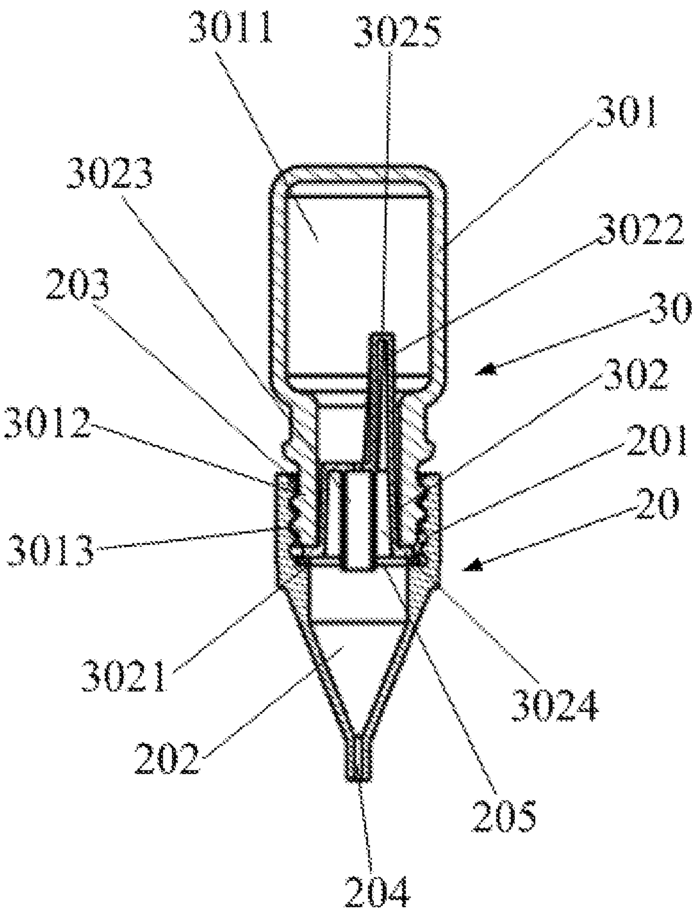
FIG. 6 is a sectional view of an essential oil bottle connected to an oiler according to Embodiment I of the present invention.
Figure 7:
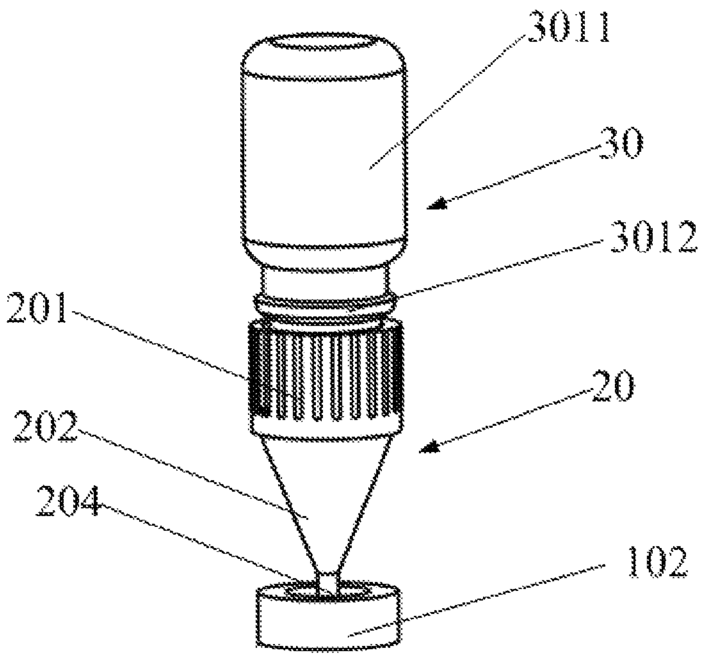
FIG. 7 is a stereogram of an essential oil bottle, an oiler and an energy conversion sheet connected in order according to Embodiment I of the present invention.
Figure 8:
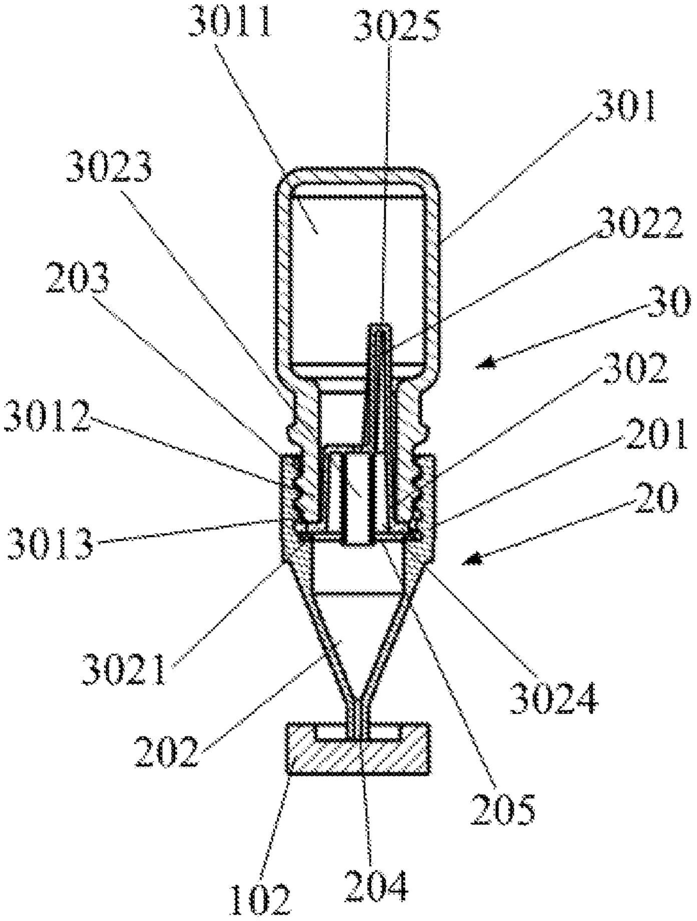
FIG. 8 is a sectional view of an essential oil bottle, an oiler and an energy conversion sheet connected in order according to Embodiment I of the present invention.

Again refer to FIG. 2 and please refer to FIGS. 5 and 6. FIG. 5 is a sectional view of an essential oil bottle, and FIG. 6 is a sectional view of an essential oil bottle connected to the oiler. The essential oil bottle 30 includes a bottle body 301 and an inner lid 302. The bottle body 301 has a cavity 3011 and a bottle mouth 3012 communicating with the cavity 3011. The cavity 3011 is used to be filled with the essential oil to be atomized. The outer wall of the bottle mouth 3012 is provided with outer threads 3013 matching the inner threads 203 of the inner wall of the connection portion 201 of the oiler 20. The inner lid 302 includes a lid portion 3021 and an air intake portion 3022 disposed at one side of the lid portion 3021. The lid portion 3021 is disposed on the bottle mouth 3012 and seals the cavity 3011. The outer threads 3013 of the outer wall of the bottle mouth 3012 is connected to the inner threads 203 of the inner wall of the connection portion 201. The sealing ring 205 is disposed between the bottle mouth 3012 and the connection portion 201. An oil outlet 3023 and an air inlet 3024 are disposed on the lid portion 3021. The oil outlet 3023 is disposed along the direction of the center axis of the lid portion 3021. The air inlet 3024 is disposed along the direction parallel to the center axis of the lid portion 3021. The two ends of the oil outlet 3023 respectively communicates with the cavity 3011 and the oil guiding cavity 202. The air inlet 3024 is disposed at one side of the oil outlet 3023 and communicates with the air intake portion 3022. The air intake portion 3022 extends to an interior of the cavity 3011 and further communicates with the interior of the cavity 3011. The side wall or the bottom of the air intake portion 3022 is provided with at least one through hole 3025 for passing air thereinto. Please refer FIGS. 7 and 8, FIGS. 7 and 8 are a stereogram and a sectional view of an essential oil bottle 30, an oiler 20 and an energy conversion 102 connected in order, respectively. When the essential oil is atomized, the essential oil flows to the oil outlet 3023 of the inner lid 302 along the inner wall of the bottle body 302 of the essential oil bottle 30 under gravity, flows to the oiler 20 from the oil outlet 3023 and flows to the nozzle 204 along the inner wall of the oil guiding cavity 202. In the process of flowing out from the nozzle 204, the air enters the air intake portion 3022 from the air inlet 3024 of the inner lid 302 of the essential oil bottle 30 and then enters the bottle body 301 from the through hole 3025 of the air intake portion 3022. When the essential oil flows to the nozzle 204, the air is blocked outside. Due to the tension, the essential oil droplets may remain in the nozzle 204 of the oiler 20 and be located on the surface of the energy conversion sheet 102. At this time, the air entering the essential oil bottle is correspondingly reduced. The bottle body 30 of the essential oil bottle 30 generates a low-pressure air, the air in the oiler 20 and the air and essential oil gravity in the bottle body 301 of the essential oil bottle 30 reach to the balance, such that the essential oil in the bottle body 301 of the essential oil bottle stops flowing out. When the energy conversion sheet 102 works and evaporates the essential oil at the nozzle 204 of the oiler 20, the air enters the air intake portion 3022 from the air inlet 3024 of the inner lid 302 of the essential oil bottle 30 again and enters the bottle body 301 from the through hole 3025 of the air intake portion 3022. The balance between the air in the oiler 20 and the air and the essential oil gravity in the bottle body 301 of the essential oil bottle 30 is broken. The air continues to enter the air intake portion 3022 from the air inlet 3024 of the inner lid 302 of the essential oil bottle 30 and enter to the bottle body 301 from the through hole 3025 of the air intake portion 3022. Under the action of its own gravity, the essential oil flows to the oiler 20 from the oil outlet 3023 of the inner lid 302 of the essential oil bottle 30 and flows out from the nozzle 204 until the nozzle 204 of the oiler 20 is blocked, and follows this cycle. When the energy conversion sheet 102 does not work, the essential oil automatically stop flowing. In this way, it may assure that the essential oil would not flow out of the bottle body 301 of the essential oil bottle 30 too much such that the surface of the energy conversion sheet 102 is covered, and it may also achieve the automatically replenishment by supplementing the essential oil from the bottle body 301 to the energy conversion sheet 102.

Figure 9:
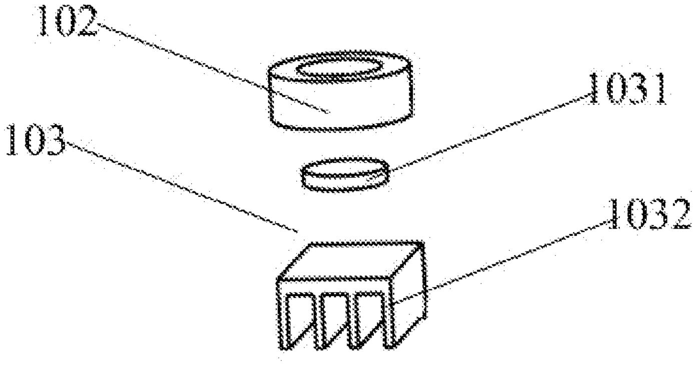
FIG. 9 is an explosion diagram of a heat sink according to Embodiment I of the present invention.
Figure 10:
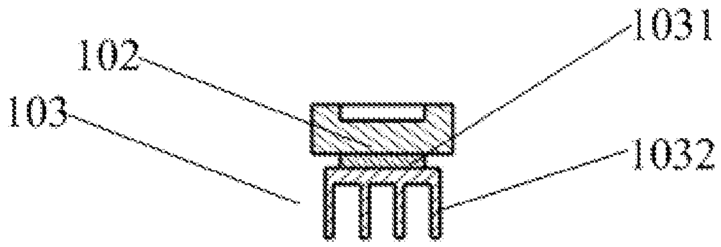
FIG. 10 is a sectional view of a heat sink according to Embodiment I of the present invention.

Refer to FIG. 2 again and please refer to FIGS. 9 and 10. FIG. 9 is an explosion diagram of the heat sink, and FIG. 10 is a sectional view of the heat sink. The ultrasonic essential oil atomizer 10 further includes a heat sink 103. The heat sink 103 includes a thermal grease 1031 and a fin radiator 1032. The thermal grease 1031 is disposed under the energy conversion sheet 102, and the fin radiator 1032 is disposed under the thermal grease 1031. Since the energy conversion sheet 102 generates a large amount of heat during working at the high frequency, in order to dissipate heat better, and control the risk of rapid temperature rise during working of the energy conversion sheet 102, the solid fin radiator 1032 is added under the energy conversion sheet 102 in the embodiment. When the energy conversion sheet 102 works, microscopically, it moves along the axial direction of the energy conversion sheet 102. In order to avoid direct contact between the fin radiator 1032 and the transducer plate 102 to affect the oscillating amplitude and to transfer and dissipate the heat of the energy conversion sheet 102, an appropriate amount of thermal grease 1031 is added to the fin radiator 1032 and the transducer plate 102. The thermal grease 1031 is a paste, does not cure at high temperatures, has a large contact surface with the energy conversion sheet 102, and facilitates the derivation of heat. By disposing the fin radiator 1032, the heat generated by the energy conversion sheet 102 is dissipated rapidly, so as to further avoid temperature rise of the energy conversion sheet 102. Additionally, the thermal grease 1031 is an insulator with a high insulation factor, and it may effectively ensure that the high frequency electrical signal may not be conducted to the space through the fin radiator 1032.

Figure 11:
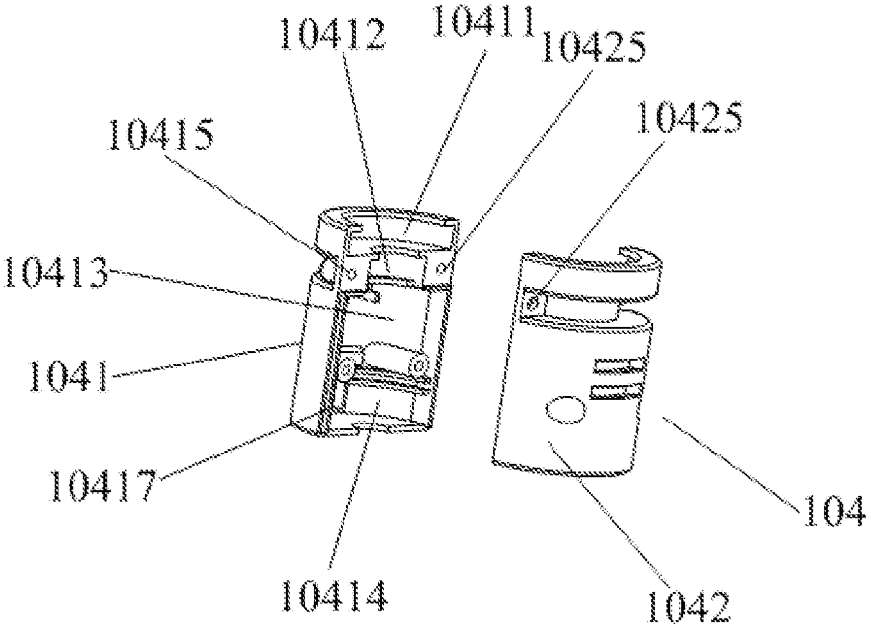
FIG. 11 is an exploded view of a housing according to Embodiment I of the present invention.

Please continue to refer FIG. 2. The ultrasonic energy conversion device 10 further includes a bracket 40 and a housing 104. The bracket 104 includes a supporting portion 401 and a limiting portion 403 connected to the supporting portion 401 through multiple supporting columns 402. The connection portion 201 of the oiler 20 is disposed inside the supporting portion 401. The oil guiding cavity 202 of the oiler 20 passes through the supporting portion 401 and extends to the limiting portion 403. Please refer to FIG. 2 again and refer to FIG. 11. FIG. 11 is an exploded view of a housing 104. The housing 104 includes a first case 1041 with hollow semi-cylindrical and a second case 1042 with hollow semi-cylindrical oppositely disposed. The first case 1041 is provided with a first seat 10411, a second seat 10412, a third seat 10413 and a fourth seat 10414 in order from top to bottom. Two sides of the second seat 10412 are respectively provided with a first fixing hole 10415 and a second fixing hole 10416. Two ends of the casing wall of the first case 1041 are respectively provided with a block 10417. The second housing 1042 is provided with a fifth seat 10421, a sixth seat 10422, a seventh seat 10423 and a eighth seat 10424 respectively corresponding to the first seat 10411, the second seat 10412, the third seat 10413, and the fourth seat 0414 from top to bottom. Two sides of the sixth seat 10422 are respectively provided with a third fixing hole 10425 and a fourth fixing hole 10426 respectively corresponding to a first fixing hole 10415 and a second fixing hole 10416. Two ends of the casing wall of the second case 1042 are respectively provided with a seat slot 10427. When the first case 1041 and the second case 1042 are connected, the blocks 10417 of the first case 1041 is disposed in the seat slot 10427 of the second case 1042. The first fixing hole 10415 and the third fixing hole 10425 are connected by screws. The second fixing hole 10416 and the fourth fixing hole 10426 are connected by screws. The first seat 10411 and the fifth seat 10421, the second seat 10412 and the sixth seat 10422, the third seat 10413 and the seventh seat 10423 and the fourth seat 10414 and the eighth seat 10424 are connected in order, so as to form a hollow cylinder cavity. The limiting portion 403 is disposed inside the first seat 10411 and the fifth seat. The energy conversion sheet 102 is disposed inside the second seat 10412 and the sixth seat 10422. The heat sink 103 is disposed inside the third seat 10413 and the seventh seat 10423. The driving circuit 101 is disposed inside the fourth seat 10414 and the eighth seat 10424.

In the embodiment, the operation principle of the ultrasonic essential oil atomizer is as follows. When the essential oil is atomized, the essential oil flows to the oil outlet 3023 of the inner lid 302 along the inner wall of the bottle body 302 of the essential oil bottle 30 under gravity, flows to the oiler 20 from the oil outlet 3023 and flows to the nozzle 204 along the inner wall of the oil guiding cavity 202. In the process of flowing out from the nozzle 204, the air enters the air intake portion 3022 from the air inlet 3024 of the inner lid 302 of the essential oil bottle 30 and then enters the bottle body 301 from the through hole 3025 of the air intake portion 3022. When the essential oil flows to the nozzle 204, the air is blocked outside. Due to the tension, the essential oil droplets may remain in the nozzle 204 of the oiler 20 and be located on the surface of the energy conversion sheet 102. At this time, the air entering the essential oil bottle is correspondingly reduced. The bottle body 30 of the essential oil bottle 30 generates a low-pressure air, the air in the oiler 20 and the air and essential oil gravity in the bottle body 301 of the essential oil bottle 30 reach to the balance, such that the essential oil in the bottle body 301 of the essential oil bottle stops flowing out. The driving circuit 101 is connected to the working voltage below 8V. The starting switch 1011 inputs the starting signal. The controlling chip 1014 outputs the high frequency signal to the energy conversion sheet high frequency oscillating circuit 1013. The energy conversion sheet high frequency oscillating circuit 1013 converts the high frequency signal to the mechanical energy, such that the energy conversion sheet 102 oscillates and evaporates the essential oil of the nozzle 204 of the oiler 20, the air enters the air intake portion 3022 from the air inlet 3024 of the inner lid 302 of the essential oil bottle 30 again and enters the bottle body 301 from the air intake portion 3022. The balance between the air in the oiler 20 and the air and the essential oil gravity in the bottle body 301 of the essential oil bottle 30 is broken. The air continues to enter the air intake portion 3022 from the air inlet 3024 of the inner lid 302 of the essential oil bottle 30 and enter to the bottle body 301 from the through hole 3025 of the air intake portion 3022. Under the action of its own gravity, the essential oil flows to the oiler 20 from the oil outlet 3023 of the inner lid 302 of the essential oil bottle 30 and flows out from the nozzle 204 until the nozzle 204 of the oiler 20 is blocked, and this cycle continues. When the energy conversion sheet 102 does not work, the essential oil automatically stop flowing.

In summary, in the embodiment, when the energy conversion sheet 102 works, the temperature rise is low, and the balance of heat dissipation may be achieved in the air at normal temperature. The ultrasonic essential oil atomizer 1 may directly carry and atomize the water-soluble and non-water-soluble essential oils to expand the types for atomizing the essential oil. The essential oil is directly atomized into particles having a diameter of 1 to 10 u on the surface of the energy conversion sheet 102 through the cavitation. It does not rely on the inefficient working methods of the traditional heating and evaporation, and does not have a problem of blocking the low frequency ultrasonic microporous atomization sheet, the service life is long, and the continuous work is not less than 5000 hours. At the same time, since the ultrasonic essential oil atomizer 1 is a pure electronic working product, it does not use the air pump or motor with the reciprocating mechanical operation to atomize the essential oil, such that it does not generate the noise and the product volume is small. When the working voltage is 5V, a USB interface is further adopted and is incorporated with a portable power, so as to form a portable ultrasonic essential oil atomizer.

Embodiment II

Figure 12:
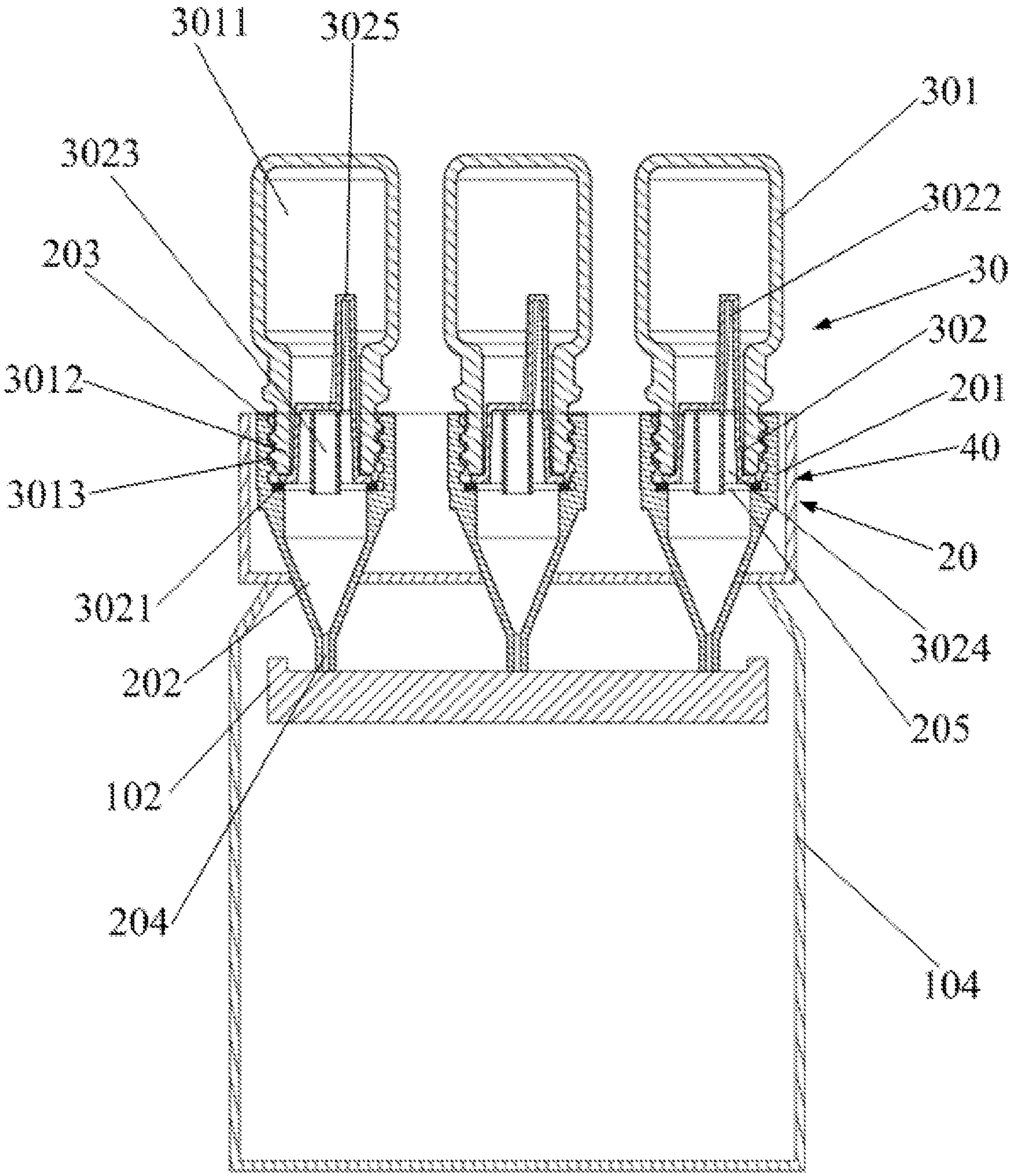
FIG. 12 is a sectional view of an ultrasonic essential oil atomizer according to Embodiment II of the present invention.

Please refer to FIG. 12, wherein FIG. 12 is a schematic structural view of an ultrasonic essential oil atomizer according to Embodiment II of the present invention. The ultrasonic essential oil atomizer of the embodiment includes an ultrasonic energy conversion device 10, a plurality of oilers 20 and a plurality of essential oil bottles 30. The ultrasonic energy conversion device 10 includes an energy conversion sheet 102 and a driving circuit 101. The structure of each of the essential oil bottles 30, each of the oilers 20 and the driving circuit is the same as Embodiment I, and the description thereof is omitted in the embodiment. In the embodiment, the nozzle 204 the oil guiding cavity 20 of each of the oilers 20 is disposed on the surface of the energy conversion sheet 102 of the ultrasonic energy conversion device 10. Further, the nozzle 204 of the oil guiding cavity 202 of each of the oilers 20 is disposed within an annular band area 1021 of 1 mm to 4 mm from the center point of the energy conversion sheet 102.

In the embodiment, in the essential oil bottles 30, the bottle body 301 of each of the essential oil bottles 30 may hold the same or different essential oil and may simultaneously atomize two or more different types of essential oils.

Embodiment II

Figure 13:
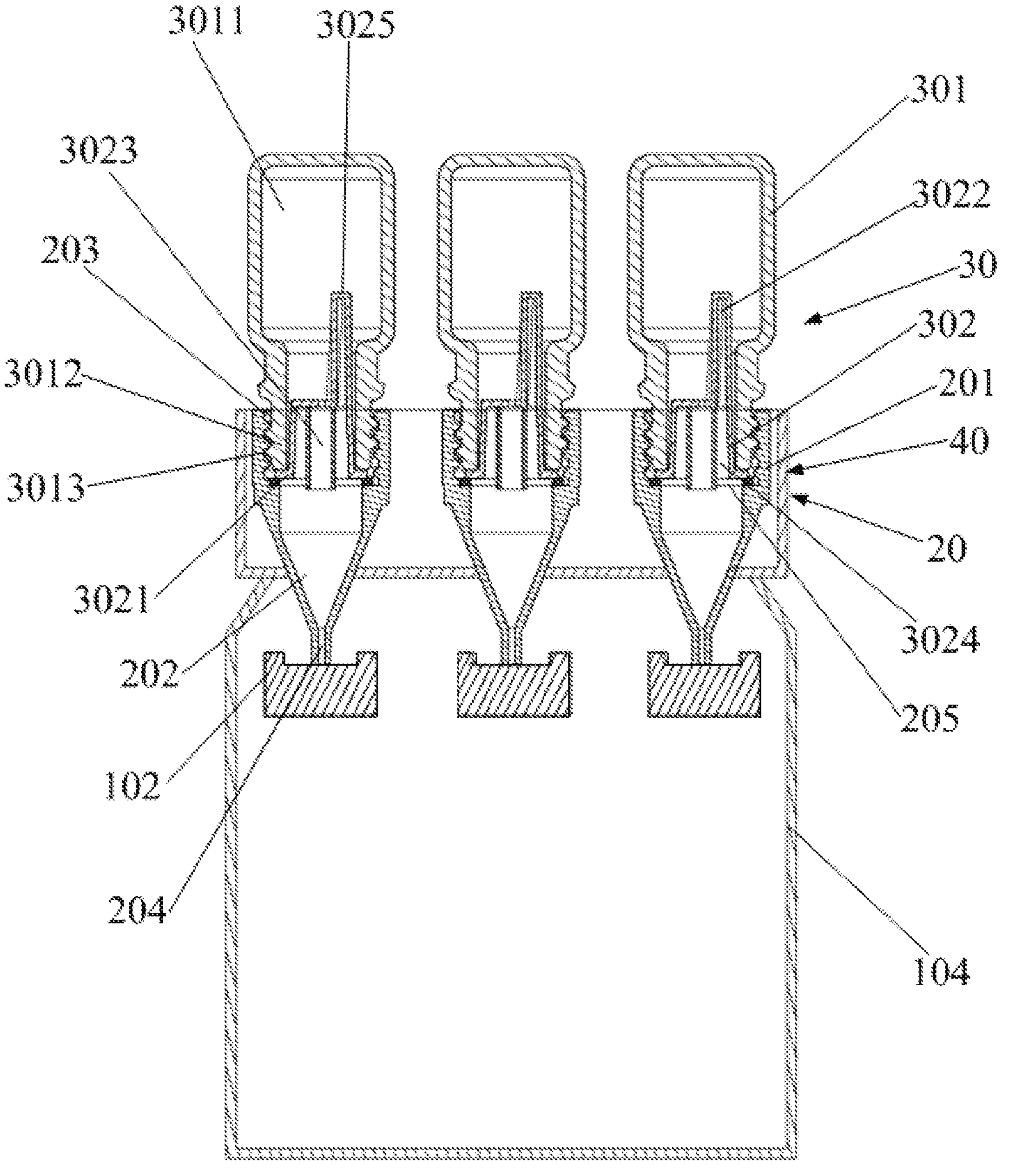
FIG. 13 is a sectional view of an ultrasonic essential oil atomizer according to Embodiment III of the present invention.
Figure 14:
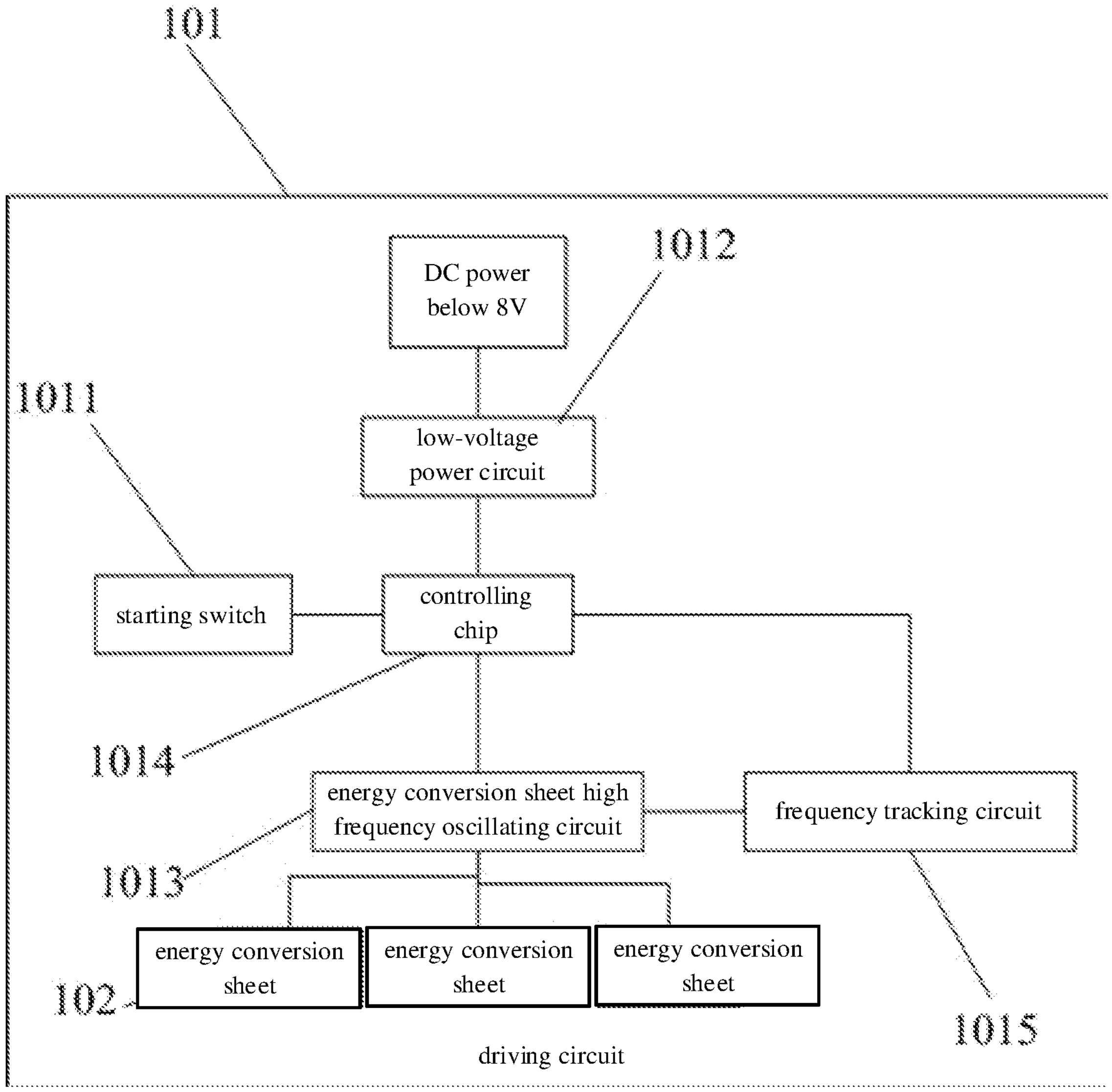
FIG. 14 is a block diagram of a driving circuit according to Embodiment III of the present invention.

Please refer to FIGS. 13 and 14. FIG. 13 is a sectional view of an ultrasonic essential oil atomizer according to Embodiment III of the present invention, and FIG. 14 is a block diagram of a driving circuit according to Embodiment III of the present invention. The ultrasonic essential oil atomizer 1 of the embodiment includes an ultrasonic energy conversion device 10, a plurality of oilers 20 and a plurality of essential oil bottles 30. The ultrasonic energy conversion device 10 includes a plurality of energy conversion sheets 102 and a driving circuit 101, wherein the driving circuit 101 is electrically connected to the energy conversion sheets, respectively, and the energy conversion sheets 102 are connected in parallel with each other. The amount of the energy conversion sheets, the oilers 20 and the essential oil bottle are identical. The structure and function of the starting switch 1011, the low-voltage power circuit 1012, the energy conversion sheer high frequency oscillating circuit 1013 and the controlling chip 1014 in the driving circuit 101 is the same as Embodiment I, the structure of each of the essential oil bottles 30 and each of the oilers 20 is the same as Embodiment, and the description thereof is omitted in the embodiment. In the embodiment, the nozzle 204 of the oil guiding cavity 202 of each of the oilers 20 is disposed on the surface of the corresponding energy conversion sheet 102 in the ultrasonic energy conversion device 10.

In the embodiment, it is the same as Embodiment II, in the essential oil bottles 30, the bottle body 301 of each of the essential oil bottles 30 may hold the same or different essential oil and may simultaneously atomize two or more different types of essential oils.

The above description is only an embodiment of the present invention, and is not intended to limit the present invention. For those skilled in the art, various modifications and changes may be made to the present invention. Any modifications, equivalent substitutions and improvements made within the spirit and principle of the present invention should be included in the scope of the claims of the present invention.

What is claimed is:

1. An ultrasonic essential oil atomizer comprising:

an ultrasonic energy conversion device, having an energy conversion sheet and a driving circuit electrically connected to the energy conversion sheet, wherein a working voltage of the driving circuit is below 8V;

at least one oiler, disposed on the ultrasonic energy conversion device and having a connection portion and an oil guiding cavity communicating with the connecting portion, wherein a nozzle is disposed at the bottom of the oil guiding cavity and the nozzle is disposed on a surface of the energy conversion sheet; and at least one essential oil bottle, having a bottle body and an inner lid, wherein the bottle body has a cavity and a bottle mouth communicating with the cavity, the inner lid comprises a lid portion and an air intake portion disposed at a side of the lid portion, the lid portion is disposed on the bottle mouth, the bottle mouth is connected to the connection portion, an oil outlet and an air inlet are disposed on the lid portion, the oil outlet communicates with the cavity and the oil guiding cavity, the air inlet is disposed at a side of the oil outlet and communicates with the air intake portion, and the air intake portion extends to an interior of the cavity and further communicates with the interior of the cavity.

2. The ultrasonic essential oil atomizer according to claim 1, wherein the ultrasonic energy conversion device further comprises a heat sink, wherein the heat sink comprises a thermal grease and a fin radiator, the thermal grease is disposed under the energy conversion sheet, and the fin radiator is disposed under the thermal grease.

3. The ultrasonic essential oil atomizer according to claim 2, wherein a distance between the nozzle and a center point of the energy conversion sheet is 1 mm to 4 mm.

4. The ultrasonic essential oil atomizer according to claim 2, wherein the ultrasonic energy conversion device comprises a housing, the housing comprises a first case and a second case oppositely disposed, the first case is provided with a first seat, a second seat, a third seat and a fourth seat in order from top to bottom, two ends of the casing wall of the first case are respectively provided with a block, the second housing is provided with a fifth seat, a sixth seat, a seventh seat and a eighth seat respectively corresponding to the first seat, the second seat, the third seat, and the fourth seat from top to bottom, two ends of the casing wall of the second case are respectively provided with a seat slot, the blocks of the first case is disposed in the seat slot of the second case, the limiting portion is disposed inside the first seat and the fifth seat, the energy conversion sheet is disposed inside the second seat and the sixth seat, the heat sink is disposed inside the third seat and the seventh seat, and the driving circuit is disposed inside the fourth seat and the eighth seat.

5. The ultrasonic essential oil atomizer according to claim 1, wherein a distance between the nozzle and the surface of the energy conversion sheet is 0.1 mm to 0.5 mm.

6. The ultrasonic essential oil atomizer according to claim 1, wherein the lid portion comprises a lid body and an oil outlet portion, wherein the lid body has an cylindrical cavity with hollow interior and a bottom lid, the bottom lid is disposed at one end of the cylindrical cavity, an air inlet and an oil outlet, the air inlet communicates with an interior of the cylindrical cavity, the oil outlet portion is disposed inside the cylindrical cavity and communicates with the oil outlet and the oil guiding cavity, respectively.

7. The ultrasonic essential oil atomizer according to claim 1, wherein the ultrasonic energy conversion device further comprises a bracket, wherein the bracket comprises a supporting portion and a limiting portion connected to the supporting portion, the connection portion of the oiler is disposed inside the supporting portion, and the oil guiding cavity of the oiler passes through the supporting portion and extends to the limiting portion.

8. The ultrasonic essential oil atomizer according to claim 1, wherein the driving circuit comprises a starting switch, a low-voltage power circuit, an energy conversion sheet high frequency oscillating circuit and a controlling chip, and the starting switch, the low-voltage power circuit, the energy conversion sheet high frequency oscillating circuit are respectively electrically connected to the controlling chip, wherein the low-voltage power circuit provides a direct current power to the controlling chip, the starting switch provides a starting signal, the controlling chip outputs a high frequency signal to the energy conversion sheet high frequency oscillating circuit according to the starting signal, the energy conversion sheet high frequency oscillating circuit provides a high frequency driving signal to the energy conversion sheet, and the energy conversion sheet is oscillated according to the high frequency driving signal.

9. The ultrasonic essential oil atomizer according to claim 1, wherein the oiler further comprises a sealing ring, and the sealing ring is disposed between the inner lid and the connection portion of the oiler.

10. An ultrasonic essential oil atomizer comprising:

an ultrasonic energy conversion device, having an energy conversion sheet and a driving circuit electrically connected to the energy conversion sheet, wherein a working voltage of the driving circuit is below 8V;

a plurality of oilers, disposed on the ultrasonic energy conversion device, wherein each of the oilers comprises a connection portion and an oil guiding cavity communicating with the connecting portion, a nozzle is disposed at the bottom of the oil guiding cavity and the nozzle is disposed on a surface of the energy conversion sheet; and a plurality of essential oil bottles, each of the essential oil bottles having a bottle body and an inner lid, wherein the bottle body has a cavity and a bottle mouth communicating with the cavity, the inner lid comprises a lid portion and an air intake portion disposed at a side of the lid portion, the lid is disposed on the bottle mouth, the bottle mouth is connected to the connection portion, an oil outlet and an air inlet are disposed on the lid portion, the oil outlet communicates with the cavity and the oil guiding cavity, the air inlet is disposed at a side of the oil outlet and communicates with the air intake portion, and the air intake portion extends to an interior of the cavity and further communicates with the interior of the cavity.

* * * * *